US008207733B2

(12) United States Patent
Meaney et al.

(10) Patent No.: US 8,207,733 B2
(45) Date of Patent: Jun. 26, 2012

(54) IMAGING BY MAGNETIC RESONANCE ADSORPTION, ELASTOGRAPHY AND TOMOGRAPHY

(75) Inventors: Paul M. Meaney, Hanover, NH (US); Keith D. Paulsen, Hanover, NH (US); John B. Weaver, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 824 days.

(21) Appl. No.: 12/246,259

(22) Filed: Oct. 6, 2008

(65) Prior Publication Data
US 2009/0036766 A1 Feb. 5, 2009

Related U.S. Application Data

(62) Division of application No. 10/529,451, filed as application No. PCT/US03/30577 on Sep. 26, 2003, now Pat. No. 7,439,736.

(60) Provisional application No. 60/414,617, filed on Sep. 27, 2002.

(51) Int. Cl.
*G01V 3/00* (2006.01)
(52) U.S. Cl. .......................... 324/306; 324/309; 600/411
(58) Field of Classification Search .................. 324/306, 324/307, 309, 312; 600/411.41, 430
See application file for complete search history.

(56) References Cited

U.S. PATENT DOCUMENTS

| | | | |
|---|---|---|---|
| 5,517,992 A | 5/1996 | Opsahi et al. | |
| 5,810,731 A | 9/1998 | Rudenko et al. | |
| 5,825,186 A | 10/1998 | Ehman et al. | |
| 6,486,669 B1 | 11/2002 | Sinkus et al. | |
| 6,567,688 B1* | 5/2003 | Wang | 600/430 |
| 6,583,624 B1 | 6/2003 | Muthupillai et al. | |
| 6,645,144 B1* | 11/2003 | Wen et al. | 600/437 |
| 6,974,415 B2* | 12/2005 | Cerwin et al. | 600/437 |
| 7,266,407 B2* | 9/2007 | Li et al. | 600/430 |
| 7,956,613 B2* | 6/2011 | Wald | 324/309 |
| 2002/0115924 A1 | 8/2002 | Nir | |
| 2002/0119575 A1 | 8/2002 | Collins | |
| 2009/0198127 A1* | 8/2009 | Li et al. | 600/437 |

OTHER PUBLICATIONS

Minghua, Xu, et al "RF-Induced Thermoacoustic Tomography" Second Joint EMBS-BMES Conference 2002, Conference Proceedings, 24th, Annual International Conference of the Engineering in Medicine and Biology Society, Annual Fall Meeting of the Biomedical Engineering Society, Houston, TX, Oct. 23-26, 2002, Annua, vol. 1 of 3. Conf.24, Oct. 23, 2002, pp. 1211-1212, XP010620033, ISBN: 0-7803-7612-9.

Muthupillai, et al. "Magnetic Resonance Elastography by Direct Visualization of Propagating Acoustic Strain Waves" Science, American Association for the Advancement of Science, US vol. 269, No. 5232, Sep. 29, 1995, pp. 1854-1857, XP000560135 ISSN: 0036-8075.

Weaver, John B., et al. "Magnetic Resonance Elastrography Using 3D Gradient Echo Measurements of Steady-State Motion" Medical Physics, American Institute of Physics, New York, US, vol. 28, No. 8, Aug. 2001, pp. 1620-1628, XP012011543, ISSN: 0094-2405.

(Continued)

*Primary Examiner* — Louis Arana
(74) *Attorney, Agent, or Firm* — Lathrop & Gage LLP

(57) ABSTRACT

A microwave imaging system provides superior breast imaging resolution by combining MR microwave absorption and MR-compatible microwave tomography calculations. These techniques may also be supplemented with magnetic resonance elastography techniques, for example, to facilitate quick multispectral imaging.

22 Claims, 10 Drawing Sheets

OTHER PUBLICATIONS

Schwarzmaier, H-J, et al. "Magnetic Resonance Imaging of Microwave Induced Tissue Heating" Magnetic Resonance in Medicine, Academic Press, Duluth, MN, US, vol. 33, No. 5, May 1, 1995, pp. 729-731, XP000620374, ISSN: 0740-3194.

International Search Report issued in related PCT Patent Application Serial No. PCT/US03/30577 dated Sep. 13, 2004, 7 pages.

International Preliminary Examination Report issued in related PCT Patent Application Serial No. PCT/US03/30577 dated Mar. 1, 2005, 6 pages.

Selected File History from related U.S. Appl. No. 10/529,451, dated between Jun. 14, 2006 through Jun. 13, 2008, 63 pages.

* cited by examiner

IMAGING BY MAGNETIC RESONANCE ADSORPTION, ELASTOGRAPHY AND TOMOGRAPHY

RELATED APPLICATIONS

This application is a Divisional of U.S. patent application Ser. No. 10/529,451, filed Aug. 28, 2005 now U.S. Pat. No. 7,439,736, which is a 371 National Phase Application of PCT/US03/30577, filed Sep. 26, 2003, which claimed priority to U.S. patent application Ser. No. 60/414,617, filed Sep. 27, 2002, each of which is incorporated by reference.

GOVERNMENT LICENSE RIGHTS

The U.S. Government has certain rights in this invention as provided for by the terms of Grant NIH-NCI#CA80139-01A1 awarded by the National Institutes of Health.

FIELD OF THE INVENTION

This invention relates to magnetic resonance (MR) imaging systems and microwave tomography systems. In particular, a system combines MR microwave absorption imaging with MR-compatible microwave tomography to differentiate biological tissues having different electrical properties. These techniques may also be combined with data generation in magnetic resonance elastography (MRE).

BACKGROUND

MR elastography (MRE) involves measuring motion resulting from low frequency vibration. Present MR elastography methods use a separate gradient waveform to encode the motion, for example, in the context of the Larmor equation that is used to measure tissue strain and discussed in U.S. Pat. No. 5,952,828 issued to Rossman et al. The gradient waveform may be added between the RF excitation and the readout of the echo. The resulting increased echo time has the undesirable effect of decreasing the signal amplitude, as well as increasing the imaging time.

MRE has shown promise in tissue imaging, including breast imaging. Several acquisition methods with corresponding reconstruction methods have been used to find the shear modulus of tissue in vivo. The first elastographic methods used ultrasound to measure static and dynamic displacements and the raw strain images were interpreted without reconstruction. See J. Ophir et al., "Elastography: A Quantitative Method for Imaging the Elasticity of Biological Tissues," Ultrasonic Imaging, 13:111-134 (1991); and K. J. Parker et al., "Tissue response to mechanical vibrations for 'sonoelasticity imaging,'" Ultrasound Med. Biol. 16(3):241-6(1990). The first MR elastographic method measured the local wavelengths of plane waves that were measured with a phase contrast method to ascertain the shear modulus. Since then, static MR methods have also been developed. More recently, methods have been developed that measure steady state motion instead of plane wave motion and use reconstructions of the partial differential equations for dynamic elastic motion.

All present MR-based methods use similar phase contrast methods to encode the motion of the tissue resulting from the low frequency vibrations induced in the tissue. Phase data of each voxel, i.e., a 3D pixel depicted as a 2D pixel with color/grey scale amplitude indications, is accumulated by moving the tissue in synchrony with the motion-encoding gradients. In static MR methods, the accumulated phase of each voxel reflects the amplitude of the motion. In dynamic MR methods, the accumulated phase of each voxel reflects the phase and amplitude of the tissue motion such that the accumulated phase must be acquired for several relative phases between the motion and gradients to solve for the amplitude and phase of the motion of each voxel.

All of the methods described above employ separate motion encoding gradients to accumulate the phase in each voxel.

Current methods for breast cancer detection and diagnosis are imperfect. For women under the age of 40 and for those under the age of 50 but with radiographically dense breasts, physical breast examination is the primary method of general screening. Unfortunately, physical breast examination has very low sensitivity and detects less than 20% of breast cancers that are detectable by X-ray mammography. In addition, cancers detected by physical exams tend to be at a later stage than those evident on mammographs, adversely affecting their prognosis. For younger women with dense breasts, the rates of false negatives and false positives generated by physical breast exams are even higher.

X-ray mammography has become the norm for breast cancer screening in recent years. However, X-ray mammography not only exposes subjects to ionizing radiation, but also has limited sensitivity and low positive predictive value. Conventional mammography also suffers from patient acceptance issues due to compression-related discomfort. While mammography is regarded as the single most important tool in early detection of breast cancer, it is not generally recommended for women under the age of 40 due to its limited efficacy on pre-menopausal breasts.

Thus, while contemporary screening practices have a beneficial effect on breast cancer detection, the limitations delineated above, especially among younger women, underscore the need to develop alternative methods to detect and characterize breast cancer. Many alternative strategies for breast cancer detection are currently being developed. Among them, a number of strategies for imaging the breast with microwaves are being investigated at the simulation, phantom and clinical scales. One approach maps microwave absorption by recording the thermoacoustic response induced by microwaves. In these studies, the microwave power absorbed by tissues generates heat and causes thermal expansion of the tissues, which launch pressure waves detectable by ultrasonic transducers. Results from these studies have shown millimeter spatial resolution arising from microwave irradiation at the centimeter wavelength scale. Although ultrasound detection has the advantages of wide-band response and relatively low cost, it also has considerable drawbacks, such as signal loss from attenuation, background clutter and geometric dilution resulting from the propagation distance between the target and the remotely-positioned noninvasive sensors. Alternative approaches to image the breast through non-thermally induced mechanical waves detected by ultrasonic transducers have also been investigated since the early 1990s.

In addition to ultrasonic techniques, MR methods have also been applied to detect non-thermally induced elastic waves emitted by tissues. While traditional MRI does not work well for detecting breast cancers, due to the low contrast between normal and malignant tissues, recent reports on the detection of motion-induced mechanical waves using MR techniques demonstrate the superior volumetric resolution of MR and the potential benefit of applying MR in breast cancer detection. In these studies, MR techniques are employed to record an elastic wave response and map tissue elasticity, which provide better discrimination of malignant tissues with altered electrical properties. Despite these potential advantages, MR techniques have not been applied to measure thermally-induced mechanical waves generated by microwave power absorption.

One problem inherent in thermoelastic wave induction is that the process is governed by local power absorption which in the electromagnetic case is a product of the intrinsic tissue properties (i.e., electrical conductivity) and the squared magnitude of the electric field. The time-averaged (or instantaneous) power deposition is a function of the fundamental property of the tissue, but also of extrinsic factors which shape specifics of the applied field distribution. For example, the geometry of the breast, the characteristics of the microwave radiator, and the electrical properties of both normal and pathological (if any) tissues govern the local field behavior. This problem has not been overcome in the art, and a continuing need exists to develop new systems for breast cancer detection that are safer, more effective and more comfortable than current detection tools.

Solution

The present system addresses the above and other problems, thereby advancing the state of the useful arts, by utilizing one or more imaging gradient waveforms to identify motion of the specimen in an MRE system. All of the gradients accumulate phase from motion and, consequently, may be used to encode the phase. Echo times are advantageously reduced because the imaging gradients encode a harmonic motion, as opposed to separate motion-encoding gradients. Some distortion is possible in this approach. However, the distortion of the phase caused by simultaneously encoding position and motion is minimal because the phase accumulated by the motion is small compared to the phase changes generated during frequency encoding. Imaging times for 100 Hz vibrations can be reduced by a factor of from 2 to 3 or more. Moreover, the echo times can be reduced by a factor of more than three which increases the signal to noise ratios (SNR) significantly in a positive way. There is a reduction in the sensitivity to motion so larger amplitude motions are desired. However, the increase in SNR compensates to some extent for the loss in sensitivity, even with no increase in the amplitude of the motion.

In one aspect, the system may combine MR imaging and microwave technology, namely, MR microwave absorption (MRMA) and MR-compatible microwave tomography (MRMT). These techniques may be applied separately, but are advantageously integrated in one system. One technique, MRMA, uses MR to image microwave-induced thermoelastic waves to detect tissue pathology. Utilization of MR techniques enables the localization of the wave response to tissue volumes commensurate with the size and scale necessary for breast cancer detection. The other technique, MRMT, incorporates MR-compatible microwave tomography to deconvolve the absorption response into its electromagnetic field and property constituents. The advantage of integrating MRMA and MRMT in one system is two fold. On the one hand, MRMT enables separation of material property effects from the field effects upon power absorption and facilitates, via a feedback loop to MRMA processes, a more accurate calculation of tissue electrical properties that are useful in MRMA. Symbiotically, MRMA enhances the tomographical map by supplying geometrical and anatomical data that may improve the spatial resolution of MRMT.

Microwave radiation includes a band ranging from 300 MHz to 30 GHz. These frequencies are generally useful for both MRMA and MRMT.

DETAILED DESCRIPTION OF PREFERRED EMBODIMENT

There will now be shown and described two new imaging techniques, namely, MRMA and MRMT, and their optional combination in one system. Although these two systems can be deployed independently, the preferred mode of operation is to integrate the two systems into one with the strengths of one system reinforcing areas of inherent weakness in the other. Specifically, MRMT provides field and property estimates for separating intrinsic from extrinsic effects in microwave absorption imaging. On the other hand, MRMA imaging provides geometrical/anatomical data that are useful in improving the spatial resolution of microwave tomography.

The system also facilitates using the gradient waveforms used for MRMA and/or MRMT imaging to encode motion in MRE imaging. As noted above, there is some distortion introduced into the image if the position and the motion are encoded simultaneously. However, the amount of motion is relatively small so the distortion is also small. Further, there is intrinsic arbitrariness in which direction the gradients are switched on and this can be used to help isolate the motion from other sources of phase accumulation.

Figure 1:
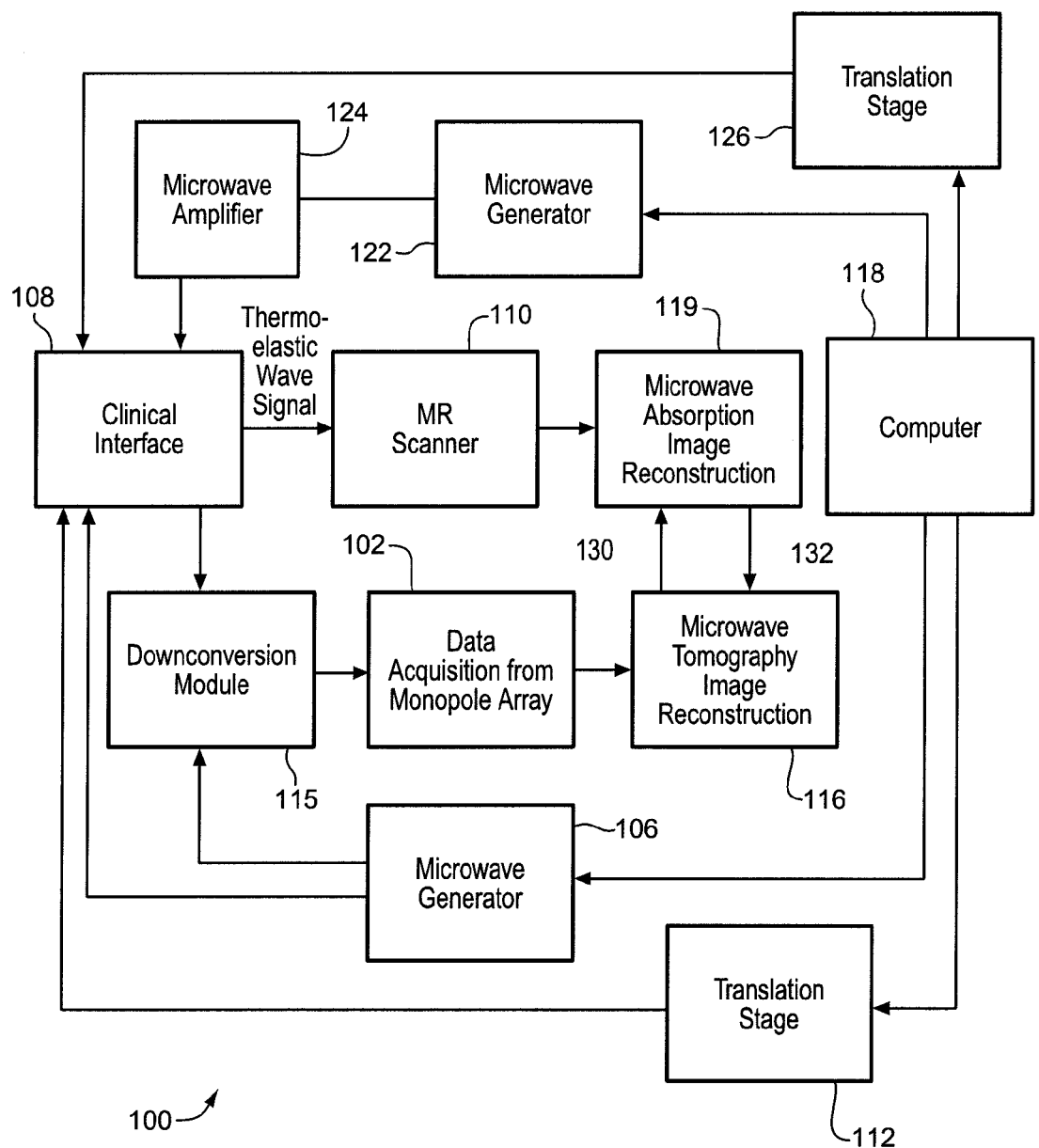
FIG. 1 is a schematic diagram depicting integration of an MR microwave absorption system and an MR-compatible microwave tomography system in accordance with one embodiment of the system.

FIG. 1 depicts a system 100 integrating MRMA and MRMT into one system. The data acquisition subsystem 102 may operate at a high frequency, for example, using signals from 300 MHz to 3 GHz transmitted by a monopole array. Use of high frequency produces high image resolution; however, ultra-high frequencies in excess of 3 GHz may have difficulty in penetrating the target tissue. A microwave generator 106 produces microwave energy which is transmitted through a clinical interface 108. The clinical interface 108 may be a receptacle designed to present a target such as a pendant human female breast for imaging analysis and may operate in association with the data acquisition subsystem 102 or an MR scanner 110. A translation stage 112 is coupled to the clinical interface 108 to control horizontal and/or vertical movement thereof.

A downconversion module 115 receives the modulated signals from the clinical interface 108 and mixes them with a reference signal from the microwave generator 106 to produce a low-frequency signal that can be collected by the data acquisition subsystem 102. Data collected by the data acquisition subsystem 102 are processed by a microwave tomography image reconstruction module 116 to yield estimates of the field and property values. A central computer 118 controls the microwave generator 106 and the translation stage 112.

In the meantime, heat-induced thermoelastic wave signals from the target 20 are detected by the MR scanner 110 which also optimally works in association with the clinical interface 108. These data from the scanner 110 are processed by a microwave absorption image reconstruction module 119. A second microwave generator 122 produces low-power microwave signals which are amplified by a microwave amplifier 124 and transmitted through clinical interface 108 to targets. A second translation stage 126 is coupled to clinical interface 108 to control the movement of microwave heating devices relative to the target tissue. Central computer 118 also controls microwave generator 122 and translation stage 126.

Feedback loops 130, 132 may be used to improve image resolution by mutually supportive MRMA-MRMT. Commencing with first estimates on the field distribution and property map, the first estimates are supplemented or enhanced by actual measurements provided by microwave tomography image reconstruction module 116 and used to iteratively update the microwave absorption image based on the latest estimates through feedback loop 130. This feedback loop 130 helps separate intrinsic and extrinsic effects on power absorption and facilitates a more accurate calculation of the electrical property of the target. This process of iteration is repeated several times to obtain more accurate values of the electrical property of the target. Secondly, the geometrical and anatomical data generated by microwave absorption image reconstruction module 119 help improve the spatial resolution of microwave tomography via feedback loop 132. Thus, the advantage of combining MRMA and MRMT is that the strength of one imaging scheme reinforces areas of inherent weakness in the other scheme by way of multiple iterations via feedback loops 130 and 132.

Figure 2:
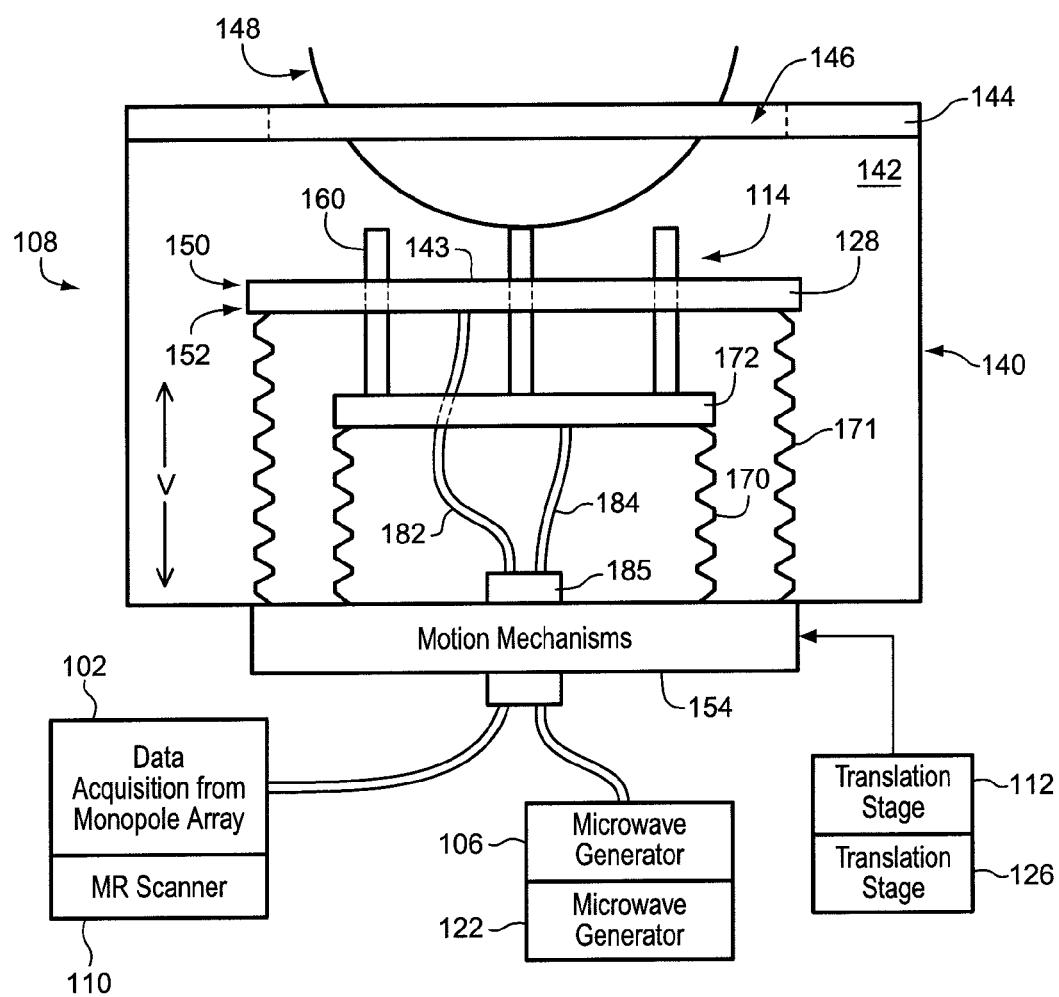
FIG. 2 depicts one embodiment of the clinical interface, including a monopole antenna mounted on a vertically movable solid array plate, and microwave high-power excitation source plate housed inside a chamber filled with fluid.

FIG. 2 depicts one embodiment of clinical interface 108, which is connected to data acquisition subsystem 102 and MR scanner 110, together with microwave generators 106, 122, and translation stages 112, 126. The clinical interface 108 contains an imaging chamber 140, coupling fluid 142, antenna array 114 and a microwave high-power excitation source plate 128. Three-dimensional movements of antenna array 114 and plate 128 are controlled by the motion mechanisms 154, for example, in the form of stepper motor-driven pinion gears (not shown) driving racks 170, 171 under the control of translation stages 112 and 126 to provide a vertical range of motion. A similar rack and pinion system (not shown) may be used to provide horizontal motion. The top surface 144 of chamber 140 contains an aperture 146, through which a human breast 148 being imaged protrudes so that breast 148 is pendant in coupling fluid 142. Space-occupation and MR-compatibility are two important factors in designing and arranging components of clinical interface 108 because these components are to be positioned in the limited space of the bore of the MRI machine.

Microwave heating from microwave high-power excitation source plate 128 can be achieved by using an embedded or surface mounted device waveguide, a microstrip spiral or a microstrip dipole antenna. The microstrip design is preferred because of its relatively smaller size. The microstrip, as embedded in the en-face "compression" (partially due to body weight) plate 128, can be integrated with a resonant gradient system 150 and/or an RE pick-up coil 152.

Microwave power generator 122 (see FIG. 1) coupled with microwave amplifier 124 having, for example, 2 kW power and 0.5-1 μsec pulse width provides sufficient degrees-of-freedom to drive the microwave illumination. Sources with higher power and broader band can also be used, but they tend to be more expensive. The power signal source and its associated parameters (repetition rate and pulse width) are broadly selectable because the thermoelastic response is not critically dependent on these parameters. While the results using high frequency (3 GHz and 9 GHz) in Wang et al. are very impressive, lower frequencies (300-450 MHz) are preferred because they provide adequate depth penetration without over exposing superficial tissues to microwave radiation. Another reason for using lower frequencies is that when MRMA is combined with MRMT, when using glycerin as coupling fluid 142, the use of higher frequencies above 500 MHz results in higher electromagnetic loss to fluid 142. Alternatively, clinical interface 108 may be implemented using phased arrays, such as a 4-quadrant array with independent power switching for heating purposes to provide the advantage of partial breast illumination. Such a design is even more preferable when MRMT is integrated with MRMA because it enables easier separation of the field effects which need to be normalized relative to the responses from other portions of the breast when simultaneous illumination is not applied.

Two predominant concerns in designing pick-up coil 152 include maximizing signal-to-noise ratio (SNR) while minimizing space-occupation. Phase contrast techniques that exploit motion encoding gradients are critically dependent on obtaining the best SNR, and proximity of coil 152 to the breast is important for coverage with the highest obtainable SNR. While "off-the-shelf" breast coils that provide vastly improved SNR and more flexible coil placement can be used, custom-designed coils such as multi-element microstrip resonator coil designs based on coupled multi-transmission line theory are preferred. By way of example, a multi-transmission line formulation of a constrained least-squares inverse modeling approach to the Biot-Savart integral may be utilized to position and optimize performance of coil 152. In its simplest form, coil 152 may feature a capacitively segmented dual-loop coil configuration having a radius and spacing that can be properly adjusted to achieve maximum SNR in fluid coupling 142.

It is both convenient and effective to place resonant gradient coil system 150 in the en-face "compression" plate 128. To optimize the coil system, the constrained least-squares inverse modeling approach to the Biot-Savart integral formulation is used to adjust the layout of the planar wire pattern so as to achieve the necessary field strength (up to 2 T/m) throughout the breast.

Because the motion caused by the microwave heating is likely small, it is preferable to use a spin echo pulse sequence or a stimulated echo as the MR pulse sequence system emanating from an integrated microwave power source comprised of microwave generator 122 and microwave amplifier 124 to maximize motion encoding time. In addition, imaging time can be reduced significantly by obtaining higher number of imaging encodes for each motion encoding period. It is desirable to increase both image encoding efficiency and motion encoding time.

The frequency distribution of the thermoelastic response contains an enormous amount of extremely valuable information regarding the size and shape of tissue features, such as lesions. Edge characteristics which are used to characterize masses in mammograms, are reflected to some extent in the spectral shape of the response. Hence, the frequency distribution of the induced thermoelastic signature is measured by changing the synchronization of the heating pulses during the motion sensitizing gradients so that new pulses commence at different phases of the gradient as the gradient progresses. This strategy increases the imaging time because one set of image volumes is required for each pattern of microwave synchronizations.

Increased image encoding efficiency becomes more important in multispectral imaging applications. It is excessively time-consuming to measure multiple motion frequencies with spin echo pulse sequences. The pulse sequence can be improved by multiplexing a number of encodement types obtained from each motion-encoded signal. For example, fast spin echo, echo planar and/or spiral scanning methods can be used to image a plurality of motion frequencies by assigning an encodement type to a particular frequency or frequency band. Moreover, the frequency of the motion-encoding gradients can be changed, and the sequence of microwave pulses can also be changed relative to the motion-encoding gradient to alter the frequency response of the motion.

In one embodiment, MRE system algorithms incorporate the assumption of tissue excitation by a sinusoidally varying mechanical vibration. In the case of MRMA, the microwave generator radiates a time-domain pulse. This pulse is transformed to the frequency-domain via a Fourier transform and has broad spectral content (i.e. it contains frequency components from across a wide frequency range). Data acquisition for MRMA using a MR machine results in the MR machine detecting information fusing a single one of those frequencies at a time. Thus, the data the MR machine produces for use in the reconstruction algorithm is from a single frequency. Because this source data is also for a single sinusoidal frequency, the source term for the MRMA algorithm is essentially the same as that in MRE—the excitation differs. So basically, there are no differences in the equations used.

The system 100 (see FIGS. 1 and 2) also provides for, methods of performing microwave tomography in an MR environment. The system elements used for MRMT include a monopole antenna array 114, motion mechanism 154 for multi-slice imaging and coupling fluid 142. One predominant consideration of the system design includes space constraint that is imposed by where the system will reside in the intended environment of use, namely, the bore of an MRI machine, such that system 100 will operate according to design parameters without interfering with the magnetic resonance function.

Figure 3:
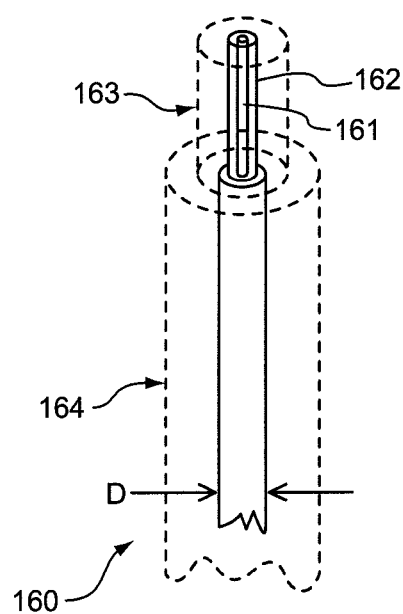
FIG. 3 is a schematic diagram of one monopole antenna design where the small diameter element of the system constructed from a thin semi-rigid coaxial cable with additional dielectric material provides structural support.

FIG. 3 shows a structure of a monopole antenna element 160, which may contain a central conductor 161 surrounded by a teflon insulator 162, an upper exposed dielectric support section 163, and a lower dielectric support 164. Monopole antenna performance, as measured in terms of characteristic impedance and radiation patterns, can be achieved using an array that contains a plurality of monopole antenna elements 160, the elements 160 presenting a range of differing diameters. A design parameter for achieving repeatable performance is that each of elements 160 has a characteristic impedance, for example, 50 Ω. The design of monopole antenna elements 160 may be modified to improve performance in an MR environment by reducing the size of metallic structures, such as central conductor 161, to reduce or eliminate MR signal artifacts. As shown in FIG. 3, the current monopole antenna design is scaled down to an outer diameter D of 2.2 mm, and non-metallic dielectric materials are used in the upper dielectric support 163 and lower dielectric support 164.

Microwave tomography of the breast is facilitated by a low contrast (as compared with the tissue) and moderately lossy coupling fluid 142 which enhances broadband operation of the transceiving antenna array and diminishes surface reflections from the breast-fluid interface that may distort image quality, especially with respect to the resolution of internal breast structure. The imaging chamber 140 is constructed to hold coupling fluid 142 into which antenna array 114 and "compression" plate 128 are inserted. Coupling fluid 142 is preferably a 70-90% glycerin solution (70-90% glycerin with 10-30% water by volume). Glycerin mixed with water has advantageous spectral properties that do not cause high electromagnetic loss at high frequencies (700 MHz to 3 GHz) within imaging chamber 140. This low attenuation is especially useful for high frequency broadband monopole antenna operation, and signal attenuation is further reduced at lower frequencies below 500 MHz. The reduced signal losses observed through glycerin and water frequencies below 500 MHz comprises an improvement relative to other possible coupling fluids and is advantageous for the MRMA system.

Figure 4:
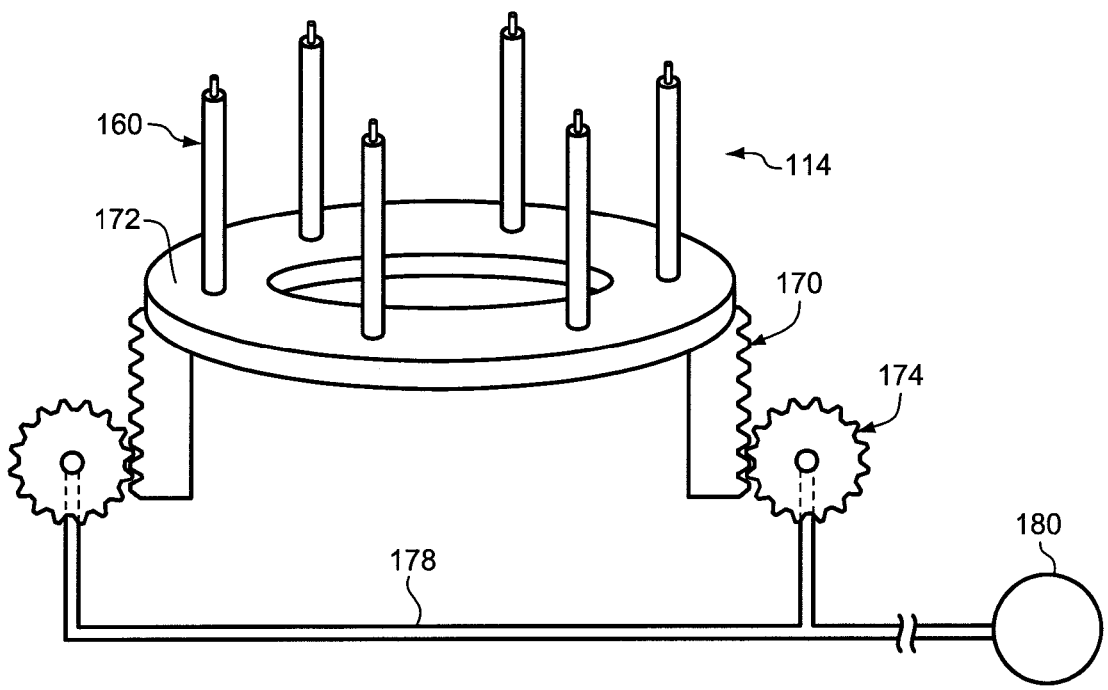
FIG. 4 is a schematic representation of a vertical array translation comprising a Plexiglas™ mounting plate with flat side gearing.

Linear translation of the antenna array 114 may be required for multi-slice imaging that encompasses a complete scan of breast 148. FIG. 4 provides information concerning one embodiment of a remotely-actuated motion mechanism 154 that provides vertical movement of antenna array 114. Antenna array 114 is fastened to a pair of rack gearing fixtures 170, which are fabricated from MR-compatible materials to minimize MR imaging artifacts. An antenna plate 172 and pinion gearing 174 may be constructed from Plexiglas material with pinion gearing 174 engaging gearing fixtures 170 to provide vertical motion. The individual gears of pinion gearing 174 are each driven through a flexible shaft 178, for example, a Bowden cable, that may be rotated manually or automatically by a remotely-positioned computer-controlled stepper motor 180. Other possible drive mechanisms (not shown) include a belt drive that couples the pinion gearing to stepper motor 180 or a plurality of such motors, placing a plurality of such motors as direct drives for each gear, or a screw drive assembly that extends and contracts with rotation of a central screw under the control of stepper motor 180.

Returning to FIG. 2, the MRMA imaging apparatus, including microwave high-power excitation source plate 128 and coil assemblies 150 and 152, are placed in coupling fluid 142 inside imaging chamber 140 for MRMT with appropriate electrical isolation, either via passage of electrical connections 182, 184 through small sealed openings 185 in the tank or via layering of an electrically insulating material such as thin coats of nonconducting epoxy over microstrip signal distribution lines (not shown). The control for the linear movement of microwave source plate 128 is similar to that for antenna array 114, for example, by substituting microwave source plate 128 for the monopole antenna array of FIG. 4. Based on the buoyancy property of the breast in glycerin and the current design of incorporating en-face "compression" plate 128 to house the microwave heating and MR coil subsystems, usually no more than 5-6 cm of vertical motion V is required.

Computer 118 may be configured with program instructions to process microwave signals from coil 152 and monopole antenna array 114. As developed originally by Kruger and later again by Wang, the time-rate of change of the electromagnetic heating rate serves as the source of a pressure wavefront propagating at the speed of sound in tissue according to the classical wave equation. See Kruger et al., "Thermoacoustic computed tomography—technical considerations," *Medical Physics*, 26:1832-1837, (1999); Kruger et al. "Thermoacoustic computed tomography technical considerations," *Medical Physics*, 26:1832-1837, (1999); Xu et al., "Microwave-induced thermoacoustic tomography using multi-sector scanning," *Medical Physics*, 28:1958-1963, (2001); Feng D et al., "Microwave-induced thermoacoustic tomography: reconstruction by synthetic aperture," *Medical Physics*, 28:2427-2432, (2001); Xu and Wang, "Signal processing in scanning thermoacoustic tomography in biological tissues," *Medical Physics*, 28:1519-1524, (2001), all of which are incorporated by reference to the same extent as though repeated herein. Through a constitutive relationship between the spatial gradient in the pressure and the mechanical displacement, the governing partial differential equation (PDE) can be recast in terms of mechanical wave propagation in a linearly elastic compressible solid driven by the electromagnetic power deposition. Hence, the image reconstruction problem is much the same as that for mechanically actuated tissue displacements in MRE, but with a different driving source of motion, for example, as described in mechanical actuation context by van Houten et al. "Initial clinical experience with steady state subzone based MR elastography of the breast," *Journal of Magnetic Resonance Imaging*, (in press) (2002) and van Houten et al. "A Three Dimensional Subzone Based Reconstruction. Algorithm for MR Elastography," *Magnetic Resonance in Medicine*, 45:827-837, (2001), which are incorporated herein by reference. Therefore, MRMA image reconstruction commences by adapting the subzone technique that is implemented for MRE. More specifically, the global mechanical interactions coupled throughout the imaging volume are converted into a set of successive, overlapping zonal (local) estimation problems which is computationally far more efficient and yet yields tissue property maps essentially at the MR voxel resolution.

Where the MRE system uses a mechanical vibration at a single frequency the MRMA may use a time-domain pulse that has an infinite number of frequencies in it. In one embodiment, after the pulse is transmitted the MR machine only collects data related to a single frequency within that range when accumulating MRMA data; however, a plurality of scans may be made at different frequencies to achieve multi-spectral resolution. MRMA data for use in the reconstruction algorithm may alternatively only use data from a single frequency that is also used in the MRE system.

Extraction of a single spectral component of transient mechanical motion through the MR phase contrast technique is sufficient to accurately reconstruct tissue elastic properties, provided the medium does not exhibit significant dispersion over the spectrum of frequencies that predominate the mechanical motion. Further, the time-rate of change of the heating electromagnetic field is orders of magnitude higher; hence, it is in a time-harmonic steady-state relative to the time-scale of the induced mechanical wavefronts which are proportional to the electromagnetic frequency multiplied by the Fourier transformed complex-valued amplitude of the electric field. As a result, the PDE in van Houten et al. "An overlapping subzone technique for MR based, elastic property reconstruction," *Magnetic Resonance in Medicine*, 42:779-786, (1999), which is incorporated herein by reference, may be modified by an additional source term that is proportional to the local time-averaged microwave power absorption to achieve spectral extraction.

MRMA image reconstruction may be implemented by first including the microwave absorption as an unknown source term and estimating its spatially-dependent value as an additional inversion parameter. This process can be implemented in several steps. Initially, the tissue elastic properties are assumed to be known and the driving source of mechanical motion is the only parameter that needs to be estimated. In another embodiment, magnetic resonance elastography data can also be collected immediately prior to MRMA excitation which can supply the spatial map of tissue elastic properties for use in MRMA image reconstruction. The algorithm can be further expanded to include mechanical property estimation. The second algorithm accepts anatomical priors derived from the MR magnitude image volume (or additional image acquisition sequence) using advanced tissue segmentation and mesh generation capabilities. The estimation of mechanical properties can be constrained to adhere to the prior segmentation, while tissue elasticity ranges can be derived from literature values for, fat and fibroglandular tissue. These elasticity constraints coupled to full freedom in terms of estimating the local power deposition make it necessary for the algorithm to emphasize the latter during data-model minimization. Maps of microwave absorption can thus be reconstructed based on this algorithm. While such maps are likely informative, their diagnostic value may be limited because the power absorption map also encodes extrinsic factors unrelated to tissue pathology. By way of example, any mapping technique, such as a multivariate correlation or neural network, may be used to relate elastic properties reconstructed directly from MRMA data to conductivity values used by the MRMT algorithm.

To address this problem, in the absence of any MRMT data (see below), the computational volume with tissue type segmentation is used to compute an electric field distribution at each iteration based on the microwave radiation and the current estimate of the electrical property map. Initially, an electromagnetic property distribution is assumed based on literature values coded to the tissue-type segmentation from the subject-specific MR image volume. This allows a 3D electric field distribution to be computed for the microwave heating field under these property assumptions. The 3D power absorption map can then be estimated from the MRMA data and used with the computed field to update the electrical conductivity distribution (the electrical permittivity will not update) and the process is repeated during the next iteration.

With regard to MRMT, algorithms may used for 2D and 3D microwave image reconstruction. By way of example, suitable algorithms are described in U.S. Pat. No. 5,841,288 issued to Meaney et al., which is hereby incorporated by reference. The most advanced of existing algorithms for microwave property reconstruction may be improved by including priors from MRMA and/or MRE-derived geometrical and anatomical information. These constraints include initial property estimates tied to pre-image-reconstruction tissue segmentation. Several approaches can then be taken for deploying the information thus obtained.

The first order constraint simply utilizes the information as a starting point for full parameter reconstruction but does not impose any requirement on the property distribution that actually evolves. The second level of constraint involves property parameter zoning based on tissue-type segmentation. This can be accomplished relatively easily and effectively by summing contributions over the relevant columns of the Jacobian matrix constructed during each property update in order to collapse regions of the mesh into zones identified by tissue-type segmentation. These boundaries are respected throughout the image reconstruction process. A third level of constraint incorporates prior anatomical information and adaptive processes respondent to the iterative property map estimate to achieve optimal reconstruction parameter reduction and degree-of-freedom placement (the latter being the important new allowance relative to the 2nd level constraint). Specifically, rather than persisting with property parameter zones defined only by MR anatomy, rezoning based on property parameter gradients that emerge subsequent to their initial deployment is allowed.

In the integrated form of imaging with both MRMA and MRMT, the algorithms for MRMT are exploited to enhance the MRMA conductivity recovery and vice versa. Specifically, the property map recovered from the initial estimate (including any priors from MR-derived anatomical data) is used to compute the 3D electromagnetic field distribution due to microwave heating which can then be incorporated with the high resolution power absorption image reconstructed from the MRMA information to produce a new high resolution map of electrical conductivity. The new conductivity map is then used to drive a better MRMT image of the electrical properties which can then be used to update the 3D field distribution of the microwave heating that can be reapplied to the MRMA power absorption image to further improve the conductivity distribution (in the case of the evolving MRMT recovery, the permittivity image as well) in an iterative fashion.

Figure 5:
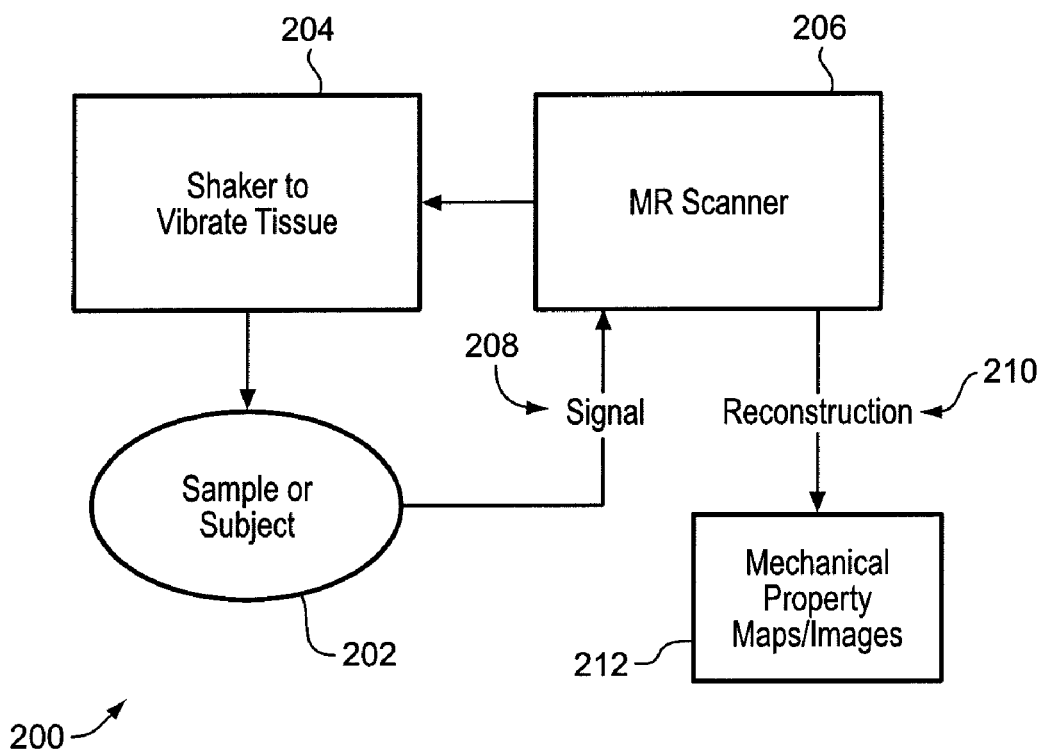
FIG. 5 is a process schematic diagram for MR elastography.

FIG. 5 illustrates an MR elastography process 200. A sample or subject 202 is placed on a shaker 204 to vibrate the tissue. The resulting displacements are measured using an MR scanner 206. In the meantime, MR phase signals 208 are collected by the scanner 206. Both sets of data are processed through a reconstruction process 210 to generate mechanical property maps and MR images 212.

Phase Distortions:

Simulations of the reconstruction of position and phase using a standard frequency encoding gradient during motion like that induced in MR elastography reveal that the magnitude and phase of the reconstructed images are perturbed by the motion especially around sharp edges but that perturbation is relatively small.

Figure 6A:
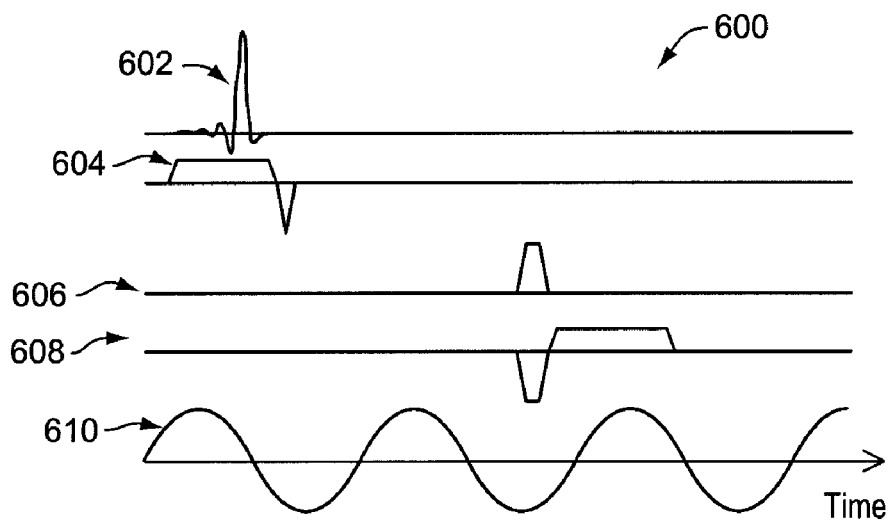
FIGS. 6A and 6B show a examples of standard MR gradient echo pulse sequences used to encode motion in the frequency encoding direction.
Figure 6B:
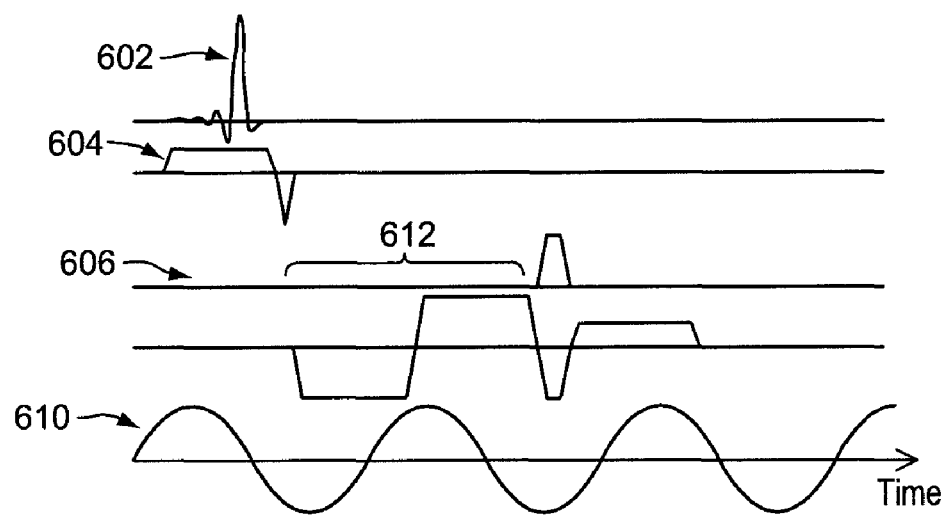

Phase Cycling:

The standard set up for MR gradient echo pulse sequences 600 consists of five functions in time as shown in FIG. 6A (without motion encoding gradient): an RF pulse 602, a slice selection pulse 604, a frequency encoding pulse 606, a phase encoding pulse 608, and the underlying wave 610 corresponding to the harmonic mechanical motion of the shaker 204. Note that while the fourth line generally refers to the phase encoding sequence, motion encoding gradients 612 are now included on this line (shown in FIG. 6B). Note that the motion encoding gradient can also be included in frequency encoding pulse 606 instead of with phase encoding pulse 608.

Figure 7A:
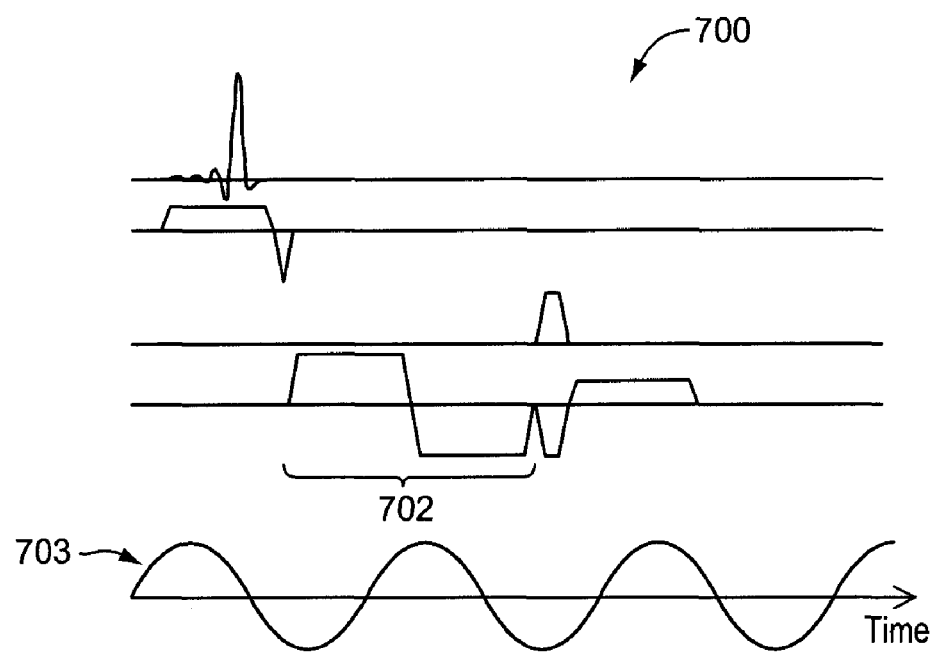
FIGS. 7A and 7B depict 3D gradient echo pulse sequences 700 and 710 that utilize a normal pulse sequence with motion encoding gradients and differ from one another in that the sign of the motion encoding gradients is positive in one-case and negative in the other.
Figure 7B:
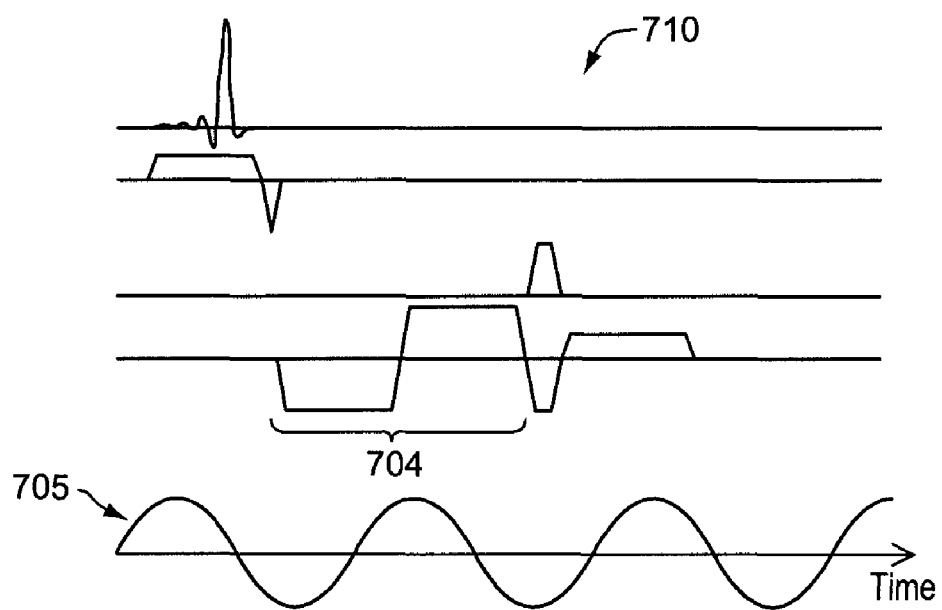

In many MR elastography measurements, the phase accumulated by the motion is isolated from other sources of phase accumulation by cycling the direction of the phase accumulated by the motion. Generally, that is done by switching the sign of the motion encoding gradient and subtracting the total phases. The phase accumulated from the motion is thereby doubled and the other phases are subtracted away. For example, two 3D gradient echo pulse sequences 700 and 710 are shown in FIGS. 7A and 7B. FIG. 7A shows a central motion encoding gradient or pulse sequence 702. FIG. 7B shows a reverse pulse sequence 704, which is the same as pulse sequence 702 except the sign of the motion encoding gradient is reversed. The phases of the images obtained from the first pulse sequence may be subtracted from the phases of the images obtained from the second pulse sequence. From the phases in the two images acquired with the two pulse sequences, the phase accumulated from the motion encoding gradient can be isolated from the other phases which is sometimes called phase cycling. To find the amplitude and relative phase of the harmonic motion, a pair of images is obtained from the pair of pulse sequences shown for multiple phases of the harmonic motion. Nothing is changed but the relative phase between the motion 703 and 705 and motion encoding gradients 702 and 704.

The same technique can be used to isolate the phase accumulated by the frequency encoding gradients and motion from the phase accumulated from the other gradients. The sign of the frequency encoding gradient can be reversed. The reconstructed image is flipped in the frequency encoding direction but that can be eliminated in the reconstruction. The phase accumulated by the motion in the frequency encoding direction is also reversed while other phases remain the same. Therefore, the phase accumulated by the frequency encoding gradient from motion in the frequency encoding direction can be isolated from other phases by subtraction. More generally, if enough different combinations of the phases accumulated from motion in the three directions and other sources of phase can be accumulated, the motion in each direction can be determined.

Figure 8A:
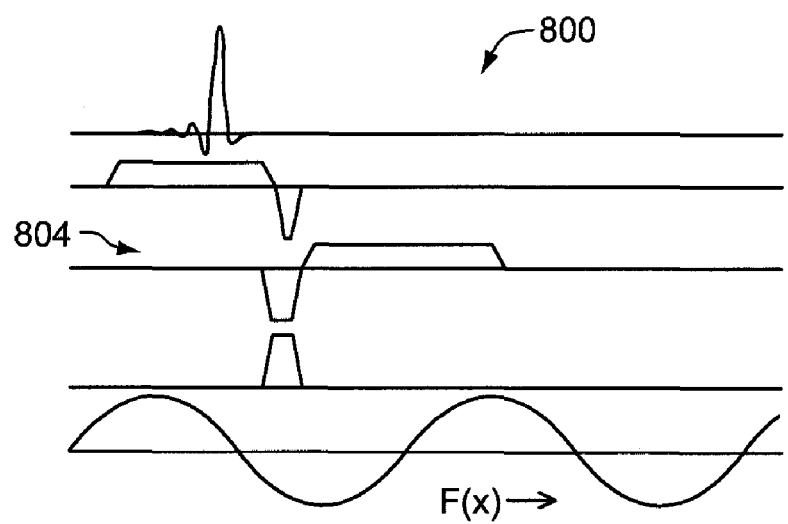
FIGS. 8A and 8B show positive and reverse pulse sequences that find motion in the frequency encoding direction and are improved with respect to FIGS. 7A and 7B.
Figure 8B:
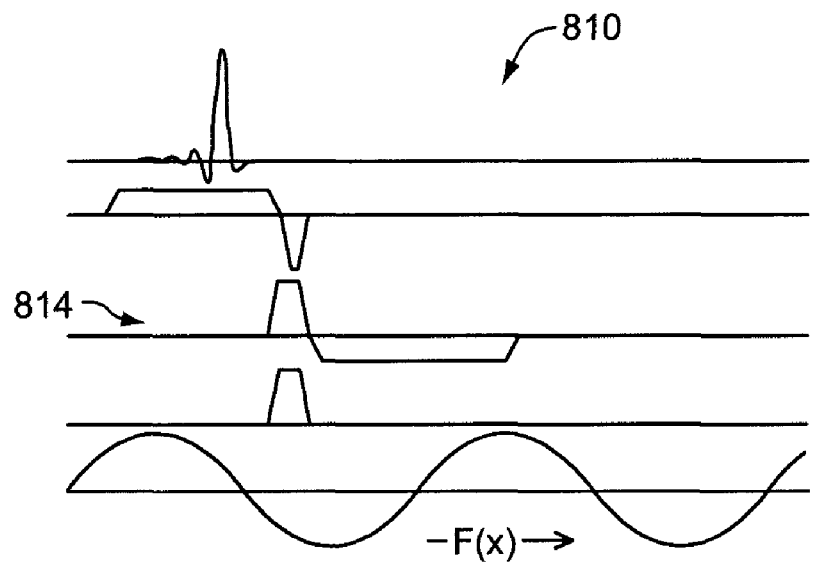

The simple case is finding motion in just the frequency encoding direction. FIGS. 8A and 8B show a pulse sequence 800 and reverse pulse sequence 810 having the sign of the frequency encoding gradients 804 and 814 reversed with respect to each other. Note that 804 and 814 are the frequency encoding gradients. The images can be combined by electronically flipping the images obtained from the second pulse sequence in the frequency encoding direction so the positions are aligned. Then the phase of each pixel is subtracted and the result is the phase accumulated from the motion in the frequency encoding direction. The echo time is reduced substantially by removing the motion encoding gradients and the total imaging time is also reduced. Because the signal decays exponentially, the signal from the pulse sequences in FIGS. 8A and B is much greater than that from FIGS. 7a and 7B. Pairs of images must still be obtained at several relative phases between the harmonic motion and the imaging gradients.

Figure 9A:
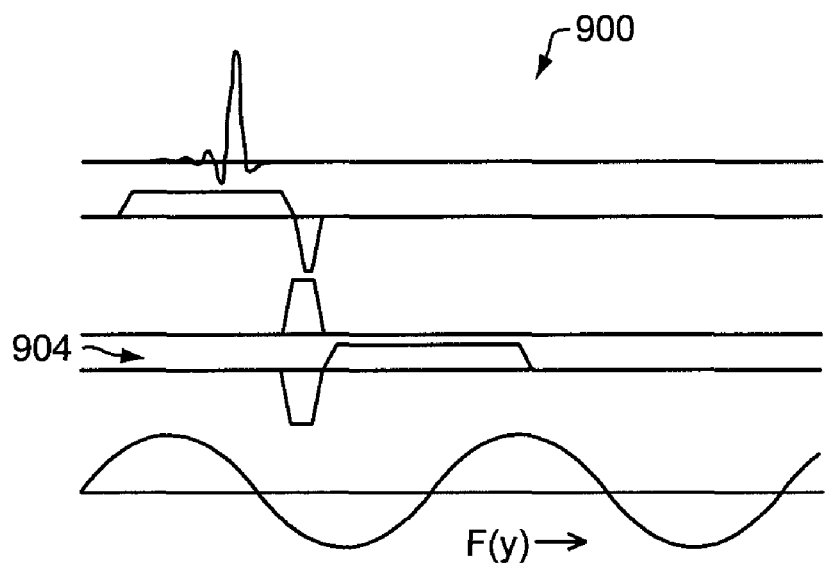
FIGS. 9A and 9B illustrate positive and reverse pulses where the phase and frequency encoding gradients are switched in comparison to FIGS. 8A and 8B.

The directions encoded by the phase and frequency encoding gradients can also be switched. So the motion in the other in-plane direction can be found using the same technique. FIG. 9A shows a pulse sequence 900 that differs from pulse sequence 800 in that the direction of the phase and frequency gradients are switched. Note that 904 and 914 are the phase encoding gradients. Pulse 904 is switched in like manner with respect to pulse 804. From the phases of the four images, it is possible to solve for the motion in all three directions.

Figure 9B:
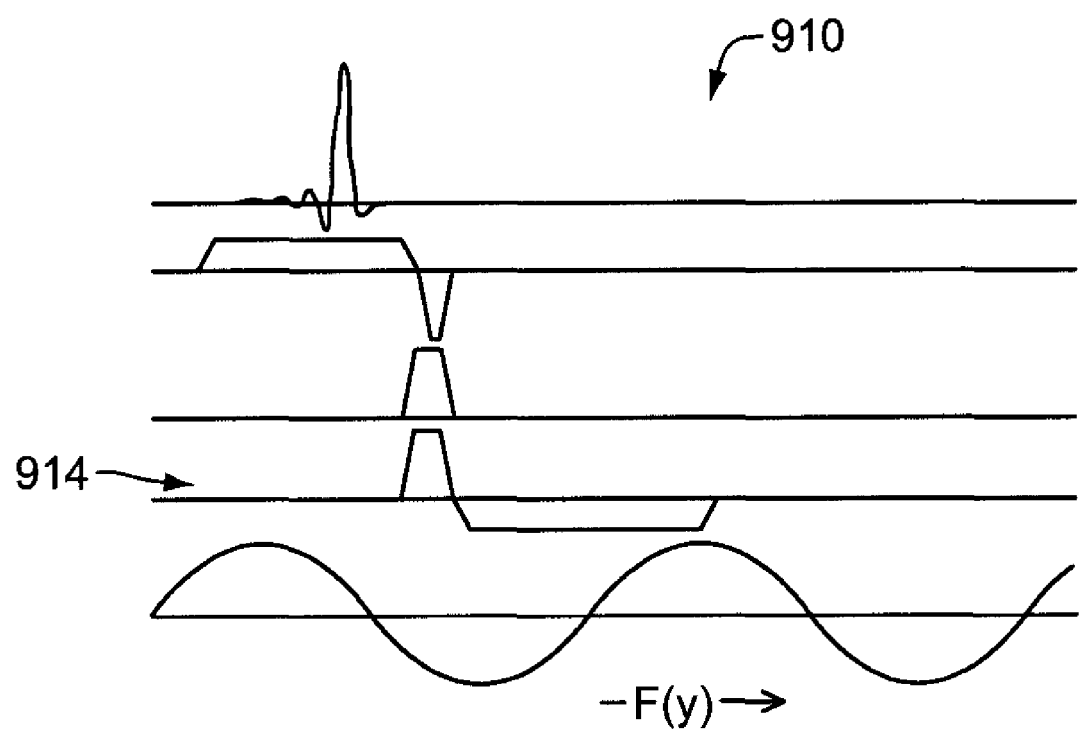

The phase accumulated by the frequency encoding gradient and the harmonic motion in the x-direction in the image shown in FIG. 8A is Fx and the phase accumulated in FIG. 8(b) is −Fx, the difference between the phases accumulated from the pair of images is 2Fx. Similarly, the phase-accumulated by the frequency encoding gradient and the harmonic in the y-direction as shown in FIG. 9(a) is Fy and that accumulated in FIG. 9(b) is −Fy, then the subtraction of the two is 2Fy. However, there is phase accumulated in all four acquisitions from the slice selection gradient and motion in the z-direction, Fz (not shown). That remains constant in all four acquisitions. It is possible to flip the sign of the slice selection gradient and subtract the two to obtain the motion in the z-direction but it is also possible to solve for the phase accumulated by motion in the z-direction from the other measurements. For example, if the average of the other four measurements were taken, Fz would add coherently and the other phases would be removed.

Figure 10:
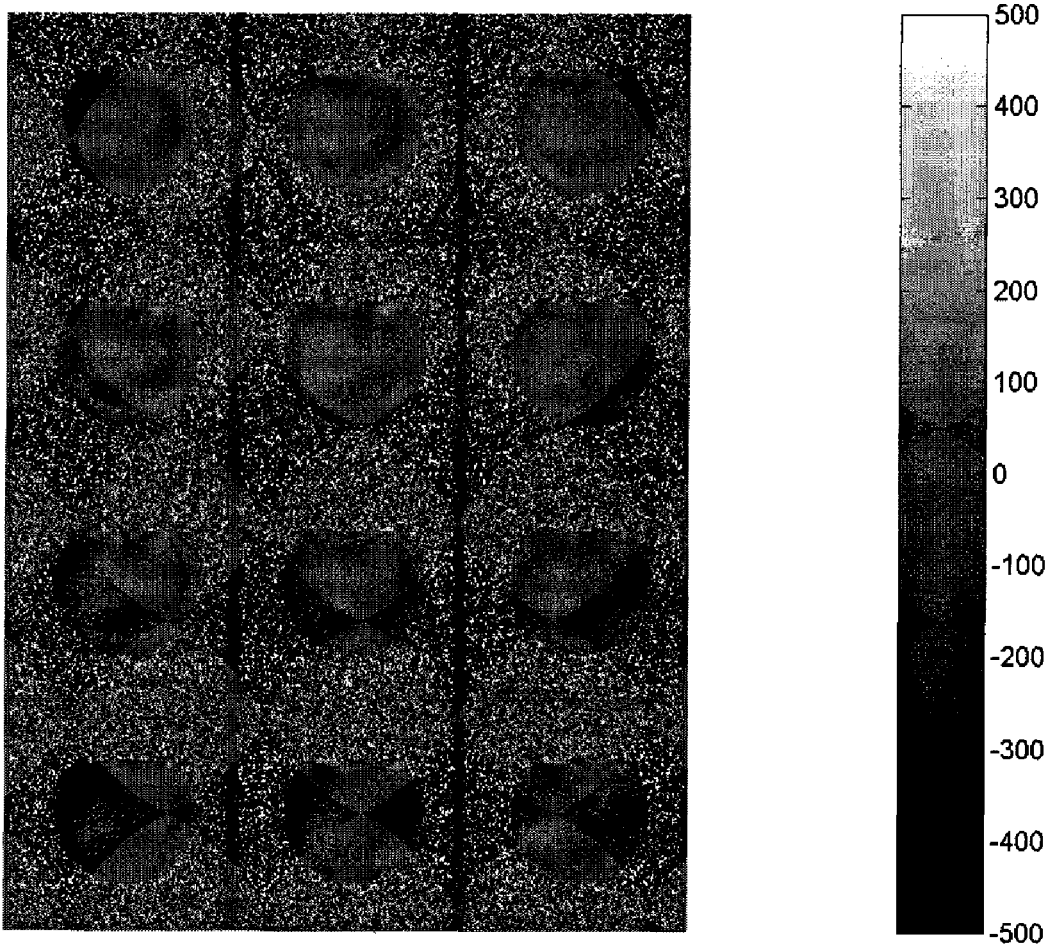
FIG. 10 is a sequence of 12 images (organized as a matrix of 4 rows of 3 images each with a legend) depicting side to side motion (x-axis of each frame) of a plastic ball filled with water (a test specimen)
Figure 11:
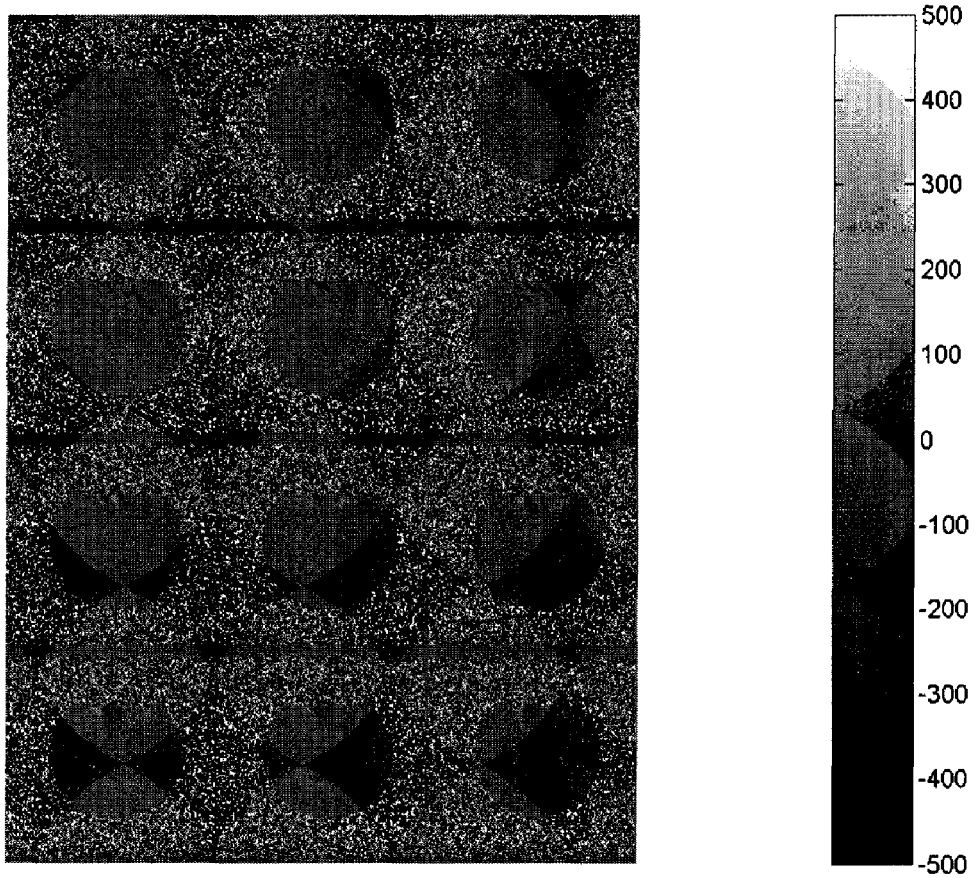
FIG. 11 shows 12 frames of the same vibrated specimen, a water filled ball, showing motion up and down (y-axis of each frame).

Exemplary Measures:

FIG. 10 is a sequence of 12 images (organized as a matrix of 4 rows of 3 images each with a legend) depicting side to side motion (x-axis of each frame) of a plastic ball filled with water (a test specimen). The ball is vibrated at about 290 Hz over a range of motion of about 30 microns. The images are 256×256 pixels covering a 12 cm field of view. FIG. 11 shows 12 frames of the same vibrated specimen, a water filled ball, showing motion up and down (y-axis of each frame). Both images are reconstructed according to the features of the system using only a single imaging gradient.

The invention claimed is:

1. A method of determining electromagnetic properties of an inhomogeneous target, comprising:
   a) repeatedly irradiating the target to be imaged with short pulses of electromagnetic energy to induce thermoelastic waves within the target;
   b) detecting mechanical displacements associated with said thermoelastic waves using a magnetic resonance (MR) scanner; and
   c) using the displacements of the thermoelastic waves with a mathematical model and tomographic data to compute the electromagnetic property distribution in said target.

2. The method of claim 1, further characterized in that frequency of the electromagnetic energy is within a range of 300 MHz to 3 GHz.

3. The method of claim 1, further comprising:
   combining an MR-compatible antenna array to determine electric field values of the inhomogeneous target in the MR environment via steps of transmitting a microwave signal through an active transmitting antenna;
   receiving said microwave signal through an active receiving antenna; and
   using said electric field values with a mathematical model to compute an electric property distribution in said target.

4. A system for determining electromagnetic properties of an inhomogeneous target, comprising:
   (a) a source for repetitively irradiating an inhomogeneous target with short pulses of electromagnetic energy to induce thermoelastic waves within the target; and
   (b) a magnetic resonance scanner for detecting the thermoelastic waves.

5. The system of claim 4, further characterized in that frequency of the electromagnetic energy is within a range of 300 MHz to 3 GHz.

6. A method of determining a three-dimensional distribution of microwave absorption of an inhomogeneous target, comprising:
   repeatedly irradiating the target to be imaged with short pulses of microwave energy from at least one transmitting antenna to induce thermoelastic waves within the target;
   detecting mechanical displacements associated with said thermoelastic waves using a magnetic resonance (MR) scanner; and
   using the detected mechanical displacements of said thermoelastic waves with a mathematical model to compute a computed distribution of microwave absorption in said target.

7. The method of claim 6, further comprising:
   obtaining a three-dimensional magnetic resonance image of the target;
   detecting regions in the magnetic resonance image; and
   using the regions in the magnetic resonance image in the mathematical model to constrain the computed distribution of microwave absorption in said target.

8. The method of claim 7 wherein the target comprises a human breast.

9. The method of claim 6, further comprising:
   using at least one antenna to apply microwave energy to the target and a plurality of antennas to measure electric fields transmitted through the target;
   using the measured electric fields and the computed distribution of the microwave absorption in a mathematical model to determine a distribution of electrical properties of the target; and
   using the distribution of electrical properties of the target to refine the computed distribution of microwave absorption of the target.

10. The method of claim 9, further comprising:
    moving at least some of the plurality of antennas from a first position to at least a second position; and
    measuring a first set of electric fields at the first position and a second set of electric fields at the second position, wherein both the first set of electric fields and the second set of electric fields are used in the mathematical model to determine a distribution of electrical properties of the target.

11. The method of claim 9, further comprising:
    obtaining a three-dimensional magnetic resonance image of the target;
    detecting tissue types of regions in the magnetic resonance image; and
    using the tissue types of regions in the magnetic resonance image in the mathematical model to constrain the computed distribution of microwave absorption in said target.

12. The method of claim 11, further comprising using the detected mechanical displacements and the computed distribution of microwave absorption in a mathematical model of elasticity to determine a distribution of elastic properties of the target.

13. The method of claim 12, further comprising using the boundaries of regions in the magnetic resonance image in the mathematical model of elasticity to constrain the computed distribution of elastic properties.

14. The method of claim 12, wherein the target comprises a human breast.

15. The method of claim 14, wherein the microwave energy is coupled into the target through a fluid comprising from seventy to ninety percent glycerin.

16. The method of claim 12, further comprising using predetermined values of mechanical properties as initial solutions for mechanical properties in said target for regions that appear in the magnetic resonance image to be fat tissue.

17. The method of claim 11, further comprising using predetermined values of electrical properties as initial solutions for electrical properties in said target for regions that appear in the magnetic resonance image to be fat tissue.

18. The method of claim 6, wherein the step of detecting mechanical displacements comprises for a plurality of selection gradients:
    generating an imaging gradient to encode position with a superimposed motion encoding pulse;
    observing a first phase of magnetic resonance response of the target;

generating an imaging gradient to select the same position with an inverted superimposed motion encoding pulse;

observing a second phase of magnetic resonance response of the target; and subtracting the first and second phase of the magnetic resonance responses of the target to provide an indicator of mechanical displacements in the target at the encoded positions.

19. The method of claim 18, further comprising using the detected mechanical displacements and the computed distribution of microwave absorption in a mathematical model of elasticity to determine a distribution of elastic properties of the target.

20. The method of claim 19, wherein the mechanical displacements are determined in each of a plurality of directions.

21. The method of claim 20, further comprising:

obtaining a three-dimensional magnetic resonance image of the target;

detecting tissue types of regions in the magnetic resonance image; and using the tissue types of regions in the magnetic resonance image in the mathematical model to constrain the computed distribution of microwave absorption in said target.

22. The method of claim 6, wherein the step of detecting mechanical displacements comprises, for a plurality of selection gradients:

generating an imaging gradient to encode position and motion, said imaging gradient comprising a positive lobe and a negative lobe having non-symmetric amplitudes;

observing a first phase of a magnetic resonance response of a target using said imaging gradient;

generating a corresponding inverted imaging gradient to image the target an additional time;

observing a second phase of a magnetic resonance response of the target; and subtracting the first and the second phase of the magnetic resonance response of the target to provide an indicator of mechanical displacements in the target at the encoded positions.

\* \* \* \* \*